United States Patent
Al-Mahmood et al.

(10) Patent No.: US 8,288,334 B2
(45) Date of Patent: Oct. 16, 2012

(54) PEPTIDES FOR WOUND HEALING

(75) Inventors: Salman Al-Mahmood, Paris (FR); Sylvie Colin, Paris (FR)

(73) Assignee: Gene Signal International SA, Lausanne (CH)

( * ) Notice: Subject to any disclaimer, the term of this patent is extended or adjusted under 35 U.S.C. 154(b) by 42 days.

(21) Appl. No.: 12/814,691

(22) Filed: Jun. 14, 2010

(65) Prior Publication Data

US 2011/0306545 A1    Dec. 15, 2011

(51) Int. Cl.
  *A61K 38/00* (2006.01)
  *A61L 15/00* (2006.01)
  *A61F 2/00* (2006.01)
  *C07K 7/00* (2006.01)
  *C07K 14/00* (2006.01)

(52) U.S. Cl. ...... 514/1.1; 514/13.3; 514/21.3; 514/21.4; 514/21.5; 514/21.6; 514/21.7; 424/423; 424/447; 530/300; 530/324; 530/325; 530/326; 530/327; 530/328

(58) Field of Classification Search .......... None
See application file for complete search history.

(56) References Cited

U.S. PATENT DOCUMENTS

| 5,155,214 A | 10/1992 | Baird et al. |
| 5,981,606 A | 11/1999 | Martin |
| 6,800,286 B1 | 10/2004 | Olwin et al. |
| 7,553,492 B2 * | 6/2009 | Al-Mahmood et al. ... 424/198.1 |
| 2008/0108551 A1 * | 5/2008 | Horobin et al. .................. 514/2 |
| 2008/0241210 A1 * | 10/2008 | Colin et al. .................. 424/423 |

FOREIGN PATENT DOCUMENTS

| EP | 0 575 484 B1 | | 9/2000 |
| WO | WO-03-029271 | * | 4/2003 |

OTHER PUBLICATIONS

Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*

* cited by examiner

*Primary Examiner* — Elizabeth C Kemmerer
*Assistant Examiner* — Regina M Deberry
(74) *Attorney, Agent, or Firm* — Young & Thompson (57) ABSTRACT

The present invention relates to new peptides, pharmaceutical composition and cosmetic composition including them and their use for wound healing.

16 Claims, 9 Drawing Sheets

SEQUENCE LISTING

```
<160> NUMBER OF SEQ ID NOS: 10

<210> SEQ ID NO 1
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 1

Thr Gln Glu Cys Pro Val Arg Thr Ser Leu Asp Arg Glu Leu Asp Leu
1               5                   10                  15

Gln Ala Ser Leu
            20

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 2

Glu Leu Asp Leu Gln Ala Ser Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 3

Val Ser Lys Asp Val Cys Arg Leu
1               5
```

```
<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Gln Ser Gln Lys Val Pro Arg Gln Val Gln Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 5

Thr Gln Glu Cys Pro Val Arg Thr Ser Leu Asp
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 6

Arg Arg Thr Thr Gln Glu Cys Pro Val Arg Thr Ser Leu Asp
1               5                   10

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
gagggcagaa tcatcacgaa                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
tgctgtcttg ggtgcattgg                                          20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
tgaaggtcgg agtcaacgga                                          20

<210> SEQ ID NO 10
<211> LENGTH: 20
<212> TYPE: DNA
<213> ORGANISM: Artificial Sequence
```

```
-continued

<220> FEATURE:
<223> OTHER INFORMATION: Synthetic Primer

<400> SEQUENCE: 10
cattgatgac aagcttcccg                                              20
```

PEPTIDES FOR WOUND HEALING

FIELD OF THE INVENTION

The present invention relates to peptides for wound healing, composition comprising said peptides and their use in both wound healing and cosmetic applications.

BACKGROUND OF THE INVENTION

Wound healing in tissues is a complex reparative process. Under normal circumstances, the process of acute wound healing can be broken down into three phases. An initial inflammatory phase, which is followed by robust tissue remodeling and proliferation (the proliferative phase), is succeeded by a maturational phase wherein re-epithelialization, dermal angiogenesis and wound closure ensues. Re-epithelialization involves the migration and proliferation of epithelial tissue, primarily keratinocytes. Angiogenesis is the growth of new blood vessels from pre-existing conduits, and is regulated by a panoply of soluble cytokines including growth factor polypeptides, as well as cell-cell and cell-matrix interactions. Chronic wounds exhibit a different healing profile from normal acute wounds in that they generally remain in an inflamed state for protracted periods of time. Non-healing wounds can most commonly be observed amongst people with diabetes, venous stasis disease, and in those patients who are immobilized. In view of the foregoing, it would be desirable to provide new biomolecules that safely and efficiently potentiate epithelial and vascular wound healing mechanisms in both acute and chronic wound healing situations. Drugs for promoting wound healing have been recently developed such as Beclapermin, a genetically engineered recombinant PDGF from Johnson & Johnson, or a pharmaceutical composition for regeneration and repair of mammalian tissues comprising PDGF and dexamethasone (EP0575484). U.S. Pat. No. 5,981,606 discloses a wound healing agent comprising TGF-beta and U.S. Pat. No. 6,800,286 and U.S. Pat. No. 5,155,214 disclose wound healing agents comprising FGF.

All already described healing agents are growth factors, cytokines or chemokines, collagen or hyaluronic acid. These agents present the drawback of inducing adverse events as they are not specific of one cellular type.

There is still a need for an alternative wound healing agent that results in an effective and rapid wound healing and does not cause adverse events.

The present invention aims to provide new peptides as alternative wound healing agent, said peptides being specific of the angiogenesis mediated by endothelial cells. Peptides, which are less than 50 amino acids, present the advantage of being an interesting tool for therapeutic use due to their small size: they offer a high affinity-specificity to their target and low toxicity profiles, a room temperature storage and better tissue penetration owing to their smaller size.

Moreover, they present the advantage of being easily synthesized compared to a full-length protein: their industrial production is thus more standardized and controlled. They do not show viral security issue as they can be chemically synthesized and do not suffer from refolding issues, glycosylation issues and activity variability.

SUMMARY OF THE INVENTION

One object of the invention is a peptide comprising one of the sequences selected in the group of SEQ ID NO: 1, SEQ ID NO: 2, SEQ ID NO: 3, SEQ ID NO: 4, SEQ ID NO: 5 and SEQ ID NO: 6. Another object of the invention is a pharmaceutical composition comprising at least one of the peptide in combination with pharmaceutically acceptable excipients.

Another object of the invention is said pharmaceutical composition for wound healing. Another object of the invention is a cosmetic composition comprising at least one of the peptide of the invention.

DETAILED DESCRIPTION OF THE INVENTION

Wound healing is based on the migration and proliferation of cells at or near the wound edge and the recruitment of new or pre-existing blood vessels to the wound site.

The inventors found out that the peptides of the invention were capable of promoting healing of wounds, through an increase of angiogenesis; and were particularly efficient.

One object of the invention is a peptide comprising one of the sequences selected in the group of SEQ ID NO: 1, SEQ ID NO: 2, SEQ ID NO: 3, SEQ ID NO: 4, SEQ ID NO: 5 and SEQ ID NO: 6. Another object of the invention is a peptide having at least 70%, 75%, 80%, 85%, 90%, 95%, 96%, 97%, 98%, 99% identity with SEQ ID NO: 1, SEQ ID NO: 2, SEQ ID NO: 3, SEQ ID NO: 4, SEQ ID NO: 5 or SEQ ID NO: 6.

```
Peptide 7:    TQECPVRTSLDRELDLQASL   (SEQ ID NO: 1)
Peptide 7B:   ELDLQASL               (SEQ ID NO: 2)
Peptide 10:   VSKDVCRL               (SEQ ID NO: 3)
Peptide 11:   QSQKVPRQVQS            (SEQ ID NO: 4)
Peptide 7A:   TQECPVRTSLD            (SEQ ID NO: 5)
Peptide 7C:   RRTTQECPVRTSLD         (SEQ ID NO: 6)
```

Another object of the invention is a peptide consisting of 8 to 50 amino acids comprising one of the sequences selected in the group of SEQ ID NO: 1, SEQ ID NO: 2, SEQ ID NO: 3, SEQ ID NO: 4, SEQ ID NO: 5 and SEQ ID NO: 6.

Another object of the invention is a peptide consisting of 8 to 40 amino acids comprising one of the sequences selected in the group of SEQ ID NO: 1, SEQ ID NO: 2, SEQ ID NO: 3, SEQ ID NO: 4, SEQ ID NO: 5 and SEQ ID NO: 6.

Another object of the invention is a peptide consisting of 8 to 30 amino acids comprising one of the sequences selected in the group of SEQ ID NO: 1, SEQ ID NO: 2, SEQ ID NO: 3, SEQ ID NO: 4, SEQ ID NO: 5 and SEQ ID NO: 6.

Another object of the invention is a peptide consisting of 8 to 25 amino acids comprising one of the sequences selected in the group of SEQ ID NO: 1, SEQ ID NO: 2, SEQ ID NO: 3, SEQ ID NO: 4, SEQ ID NO: 5 and SEQ ID NO: 6.

Another object of the invention is a peptide consisting of 8 to 20 amino acids comprising one of the sequences selected in the group of SEQ ID NO: 1, SEQ ID NO: 2, SEQ ID NO: 3, SEQ ID NO: 4, SEQ ID NO: 5 and SEQ ID NO: 6.

Another object of the invention is a peptide consisting of 8 to 18 amino acids comprising one of the sequences selected in the group of SEQ ID NO: 2, SEQ ID NO: 3, SEQ ID NO: 4, SEQ ID NO: 5 and SEQ ID NO: 6.

Another object of the invention is a peptide consisting of 8 to 16 amino acids comprising one of the sequences selected in the group of SEQ ID NO: 2, SEQ ID NO: 3, SEQ ID NO: 4, SEQ ID NO: 5 and SEQ ID NO: 6.

Another object of the invention is a peptide consisting of 8 to 14 amino acids comprising one of the sequences selected in the group of SEQ ID NO: 2, SEQ ID NO: 3, SEQ ID NO: 4, SEQ ID NO: 5 and SEQ ID NO: 6.

Another object of the invention is a peptide consisting of 8 to 12 amino acids comprising one of the sequences selected in the group of SEQ ID NO: 2, SEQ ID NO: 3, SEQ ID NO: 4, and SEQ ID NO: 5.

Another object of the invention is a peptide consisting essentially of an amino acid sequence selected in the group of SEQ ID NO: 1, SEQ ID NO: 2, SEQ ID NO: 3, SEQ ID NO: 4, SEQ ID NO: 5 and SEQ ID NO: 6.

"Peptide" as used herein refers to a polymer in which the monomers are alpha amino acids joined together through amide bonds. Peptides are two or often more amino acid monomers long, and preferably not longer than 50 amino acids. Amino acid residues in peptides are abbreviated as follows: Phenylalanine is Phe or F; Leucine is Leu or L; Isoleucine is He or I; Methionine is Met or M; Valine is Val or V; Serine is Ser or S; Proline is Pro or P; Threonine is Thr or T; Alanine is Ala or A; Tyrosine is Tyr or Y; Histidine is H is or H; Glutamine is Gin or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Stereoisomers (e.g., D-amino acids) of the twenty conventional amino acids, unnatural amino acids such as alpha,alpha-disubstituted amino acids, N-alkyl amino acids, lactic acid, and other unconventional amino acids may also be suitable components for compounds of the technology provided herein. Examples of unconventional amino acids include: beta-alanine, 1-naphthylalanine, 2-naphthylalanine, 3-pyridylalanine, 4-hydroxyproline, O-phosphoserine, N-acetylserine, N-formylmethionine, 3-methylhistidine, 5-hydroxylysine, nor-leucine, and other similar amino acids and imino acids (e.g., 4-hydroxyproline).

The peptides described herein can be produced synthetically by chemical synthesis or enzymatic synthesis as it is well known in the art. Alternatively, nucleotide sequences encoding the peptides of the invention can be introduced into a protein expression vector and produced in a suitable host organism (e.g., bacteria, insect cells, etc), then purified. An additional polypeptide ("tag") can be added on for the purpose of purifying or identifying or purifying the peptides. Protein tags make it possible, for example, for the polypeptides to be adsorbed, with high affinity, to a matrix, and for the matrix then to be washed stringently with suitable buffers without the complex being eluted to any significant extent, and for the adsorbed complex subsequently to be eluted selectively. Examples of the protein tags which are known to the skilled person are a (His)6 tag, a Myc tag, a FLAG tag, a haemagglutinin tag, a glutathione transferase (GST) tag, intein having an affinity chitin-binding tag or maltose-binding protein (MBP) tag. These protein tags can be located N-terminally, C-terminally and/or internally.

One object of the invention is the peptides as described here above, said peptides being modified.

The peptides provided herein can be modified by means well-known in the art.

For example, the peptides can be modified by the addition of one or more functional groups such as phosphate, acetate, or various lipids and carbohydrates. The peptides of the invention can also exist as peptide derivatives. The term "peptide derivative" refers to compound having an amino group (—NH—), and more particularly, a peptide bond. Peptides may be regarded as substituted amides. Like the amide group, the peptide bond shows a high degree of resonance stabilization. The C—N single bond in the peptide linkage has typically about 40 percent double-bond character and the C=O double bond about 40 percent single-bond character. "Protecting groups" are those groups that prevent undesirable reactions (such as proteolysis) involving unprotected functional groups. Specific examples of amino protecting groups include formyl; trifluoroacetyl; benzyloxycarbonyl; substituted benzyloxycarbonyl such as (ortho- or para-) chlorobenzyloxycarbonyl and (ortho- or para-) bromobenzyloxycarbonyl; and aliphatic oxycarbonyl such as t-butoxycarbonyl and t-amiloxycarbonyl. The carboxyl groups of amino acids can be protected through conversion into ester groups. The ester groups include benzyl esters, substituted benzyl esters such as methoxybenzyl ester; alkyl esters such as cyclohexyl ester, cycloheptyl ester or t-butyl ester. The guanidino moiety may be protected by nitro; or arylsulfonyl such as tosyl, methoxybenzensulfonyl or mesitylenesulfonyl, even though it does not need a protecting group. The protecting groups of imidazole include tosy, benzyl and dinitrophenyl. The indole group of tryptophan may be protected by formyl or may not be protected.

The modification of the peptides aims in particular to improve their life time in vivo. One type of modification is the addition to the N or C termini of the peptides of polyethylene glycol (PEG). PEG is known by the person skilled in the art to have many properties that make it an ideal carrier for peptides such as high water solubility, high mobility in solution and low immunogenicity. This modification also protects the peptides from exopeptidases and therefore increases their overall stability in vivo.

The other modifications used to prevent degradation of the peptides by endopeptidases or exopeptidases include N-terminal modifications such as acetylation or glycosylation, C-terminal modifications such as amidation and use of unnatural amindo acids (β-amino and α-trifluoromethyl amino acids) at particularly sites within the peptides.

Another alternative to increase peptide molecular size is the genetic fusion of the peptides to the Fc domain of human gamma immunoglobulin or the fusion of the peptides to albumin.

Another object of the invention is a pharmaceutical composition comprising at least one of the peptide as described here above in combination with pharmaceutically acceptable excipients.

Another object of the invention is a method for wound healing comprising the administration to a subject in need thereof of a therapeutically effective amount of at least one of the peptides of the invention.

According to the invention, the subject may be any mammal, preferably a human.

"Therapeutically effective dose or amount" refers to a dosage level sufficient to induce a desired biological result. That result can be alleviation of the signs, symptoms, or causes of a disease, or any other desired alteration of a biological system. Preferably, this dose or amount will be sufficient to stimulate or augment the epithelial and/or endothelial wound healing response and, thus, induce or potentiate wound healing.

The term "pharmaceutically acceptable" refers to compounds and compositions which may be administered to mammals without undue toxicity. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like.

In one embodiment, the composition may comprise a pharmaceutically acceptable salt of the peptide.

Examples of the pharmaceutically acceptable salt include salts with inorganic bases, salts with organic bases, salts with inorganic acids, salts with organic acids, salts with basic or acidic amino acids and the like. Examples of the salt with an inorganic acid include alkali metal salts, such as a sodium salt and a potassium salt; an alkaline earth metal salt such as a calcium salt and a magnesium salt; an aluminum salt; and an ammonium salt. Examples of the salt with an organic base include salts with trimethylamine, triethylamine, pyridine, picoline, 2,6-lutidine, ethanolamine, diethanolamine, triethanolamine, cyclohexylamine, dicyclohexylamine and N,N'-dibenzylethylenediamine. Examples of the salt with an inorganic acid include salts with hydrochloric acid, boric acid, nitric acid, sulfuric acid and phosphoric acid. Examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid. Examples of the salt with a basic amino acid include salts with arginine, lysine and ornithine. Examples of the salt with an acidic amino acid include salts with aspartic acid and glutamic acid. The list of suitable salts is disclosed in Remington's Pharmaceutical Sciences, 17th ed., Mack Publishing Company, Easton, Pa., p 1418, 1985, the entire disclosure of which is incorporated herein by reference.

As used herein, the term "wound healing" refers to augmenting, improving, increasing, or inducing closure, healing, or repair of a wound. Wound healing is considered to be promoted, for example, if the time of healing a wound treated with the peptide of the invention compared to a wound not treated with the peptide of the invention is decreased by about 10%, preferably decreased by about 20%, 25%, 30%, 40%, more preferably decreased by about 50%, and most preferably decreased by about 75%. Conversely, the degree of scar formation can be used to ascertain whether wound healing is promoted.

The wound can be an internal wound or an external wound found in any location of a mammal. A wound is a type of physical trauma where the integrity of the skin or tissue is disrupted as a result from i.e. external force, bad health status, aging, exposure to sunlight, heat or chemical reaction or as a result from damage by internal physiological processes. If the outer layer of a tissue is damaged the wound is considered an open wound.

Wounds can also be caused by surgical procedures, such as open heart surgery, organ transplants, amputations, and implantations of prosthetics, such as joint and hip replacement, etc.

The wound can be an open wound or closed wound.

Open wounds refers to wounds in which the skin is broken. Open wounds include, for example, incisions (i.e., wounds in which the skin is broken by, for instance, a cutting instrument (e.g., knife, razor, etc.)), lacerations (i.e., wounds in which the skin is typically broken by a dull or blunt instrument), abrasions (e.g., generally a superficial wound in which the topmost layers of the skin are scraped off), puncture wounds (typically caused by an object puncturing the skin, such as nail or needle), penetration wounds (e.g., caused by an object such as a knife), and gunshot wounds.

Closed wounds are typically wounds in which the skin is not broken. Closed wounds include for example contusions (or bruises) caused by a blunt force trauma that damages tissue under the skin, hematomas caused by damage to a blood vessel that in turn causes blood to collect under the skin, crush injury caused by a great or extreme amount of force applied over a long period of time, acute and chronic wounds.

Non-limitative examples of wounds are:
a burn wound is the injury resulting from exposure to heat, electricity, radiation (for example, sunburn and laser surgery), or caustic chemicals,
skin wounds due to aging or the environment, this includes for example splits, dry skin, roughness of the skin and the like,
wounds due to external force damaging the tissue,
ulcers (lesion on the surface of the skin or a mucous surface),
wounds in Diabetes Mellitus are typically foot injuries due to numbness caused by nerve damage (diabetic neuropathy) and low blood flow to the legs and feet. The most serious injury is a foot ulcer. Diabetic foot ulcers are at very high risk of becoming infected, and sometimes they cannot be healed. Non-healing foot ulcers are a frequent cause of amputation in people with diabetes,
decubitus wounds, decubitus (bedsores), i.e. lesions caused by unrelieved pressure to any part of the body, especially portions over bony or cartilaginous areas.

In one embodiment of the invention, the pharmaceutical composition as described here above is for wound healing.

In one embodiment of the invention, the composition of the invention is for treating acute or chronic wounds.

Acute wounds are caused by external damage to intact skin and may be classified into different types, according to the object that caused the wound: for example, incisions or incised wounds, lacerations, abrasions and grazes, burns, puncture wounds caused by an object puncturing the skin, such as a nail or a needle, penetration wounds caused by an object such a knife entering the body, gunshot wounds caused by a bullet or similar projectile driving into or through the body. Acute wounds may also be closed wounds, such as contusions or bruises, hematoma, crushing injuries caused by a great or extreme amount of force applied over a long period of time. Other acute wounds are due to dermatologic diseases such as psoriasis, acne and eczema.

Chronic wounds are most frequently caused by endogenous mechanisms associated with a predisposing condition that ultimately compromises the integrity of dermal or epithelial tissue. Common chronic wounds are venous ulcers, which usually occur in the legs and mostly affect the elderly, diabetic ulcers which is another major cause of chronic wounds, pressure ulcers, which usually occur in people with conditions such as paralysis that inhibit movement of body parts that are commonly subjected to pressure such as the heels, shoulder blades and sacrum, corneal ulcers, most commonly caused by an infection with bacteria, viruses, fungi or amoebae, and digestive ulcers. Other types of chronic wounds may be due to causes such as ischemia and radiation poisoning. All chronic wounds heal slowly and in an unpredictable manner. The wound may relate to any tissue such as for example the eye, mucuous, lung, kidney, heart, gut, tendons, liver or vascular tissues, such as for example veins, venules, arteries, and capillaries.

According to the invention, the peptides of the invention present the advantage of activating angiogenesis and thereby promote healing of wounds.

Another object of the invention is a cosmetic composition comprising at least one of the peptides of the invention. This composition is for cosmetic application: for example prevention of aging of the skin, cellulites, dry skin, splits, or treatment of oral aphtous lesions, burning mouth syndrome . . . .

According to the invention, the peptides of the invention may be administered orally, topically, or by parenteral means, including subcutaneous, transdermal or intramuscular injection, implantation of sustained release depots, intravenous injection, intranasal administration, and the like.

According to the invention, the compositions comprising the peptides of the invention may be aqueous solutions, emulsions, creams, ointments, suspensions, gels, liposomal suspensions, and the like.

Examples of compositions for topical administration include, but are not limited to, lotion, salve, gel, cream, balsam, tincture, cataplasm, elixir, paste, spray, collyrium, drops, suspension, dispersion, hydrogel, ointment, emulsion or powder comprising at least one of the peptide of the invention.

Other topical formulations include aerosols, bandages, dressing materials, alginate dressing and other wound dressings.

Oral formulations include, but are not limited to, drinkable suspension or solution, syrup, tablets, capsules, pills . . . .

Alternatively one may incorporate or encapsulate the peptide of the invention in a suitable medical device, for implantation near the site to be treated locally.

According to the invention, the medical device may be in the form of a transdermic medical device, a controlled drug release medical device or a drug-eluting stent. Transdermic medical device refers to a device for slow liberation via transdermic process of the peptide of the invention (for example an adhesive patch). A drug eluting stent refers to a stent that has been coated with the peptides of the invention.

In a particular embodiment of the invention, the peptides of the invention are comprised into medical device such as absorbent or adsorbent products. Suitable absorbent or adsorbent products, for example, are capable of absorbing or adsorbing a wound fluid when applied at a wound site. Examples of said products include, for example, bandages, gauzes, wound or sore dressings, dermal patches and adhesive tapes. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), chitosan based dressings, calcium alginates (nonwoven composites of fibers from calcium alginate), and cellophane (cellulose with a plasticizer). Specifically contemplated is the use of liquid absorbent products where the peptides of the invention are impregnated within or attached (covalently or otherwise) to the surface of the product.

According to the invention, the composition comprises the peptide of the invention in an amount of about 0.0001 to 500 mg of the peptide per milliliter or gram of the composition, preferably from about 0.001 to 50 mg, more preferably from 0.01 to 5 mg and even more preferably from 0.1 to 1 mg of the peptide per milliliter or gram of the composition.

According to the invention, the composition comprises the peptide of the invention in an amount from about 0.01% to 90% by weight, preferably from 0.1 to 10% by weight, more preferably from 1 to 5% by weight.

In another embodiment of the invention, the composition comprising at least one of the peptides of the invention may further comprise at least one other wound healing agent.

In another embodiment of the invention, the composition comprising at least one of the peptides of the invention may be used in combination with at least one other wound healing agent.

Such other wound healing agent include, without being limited to, growth factors, cytokines, enzymes, and extracellular matrix components. For example, collagenase treatment of the sub-endothelial extracellular matrix in combination with the peptides of the invention may synergistically accelerate endothelial migration and proliferation to a level greater than the inductive influence of collagenase treatment in the absence of peptides.

Agents that effect wound repair can also be included in such a composition to augment the wound healing process. Such agents include members of the family of growth factors, such as insulin-like growth factor (IGF-1), platelet derived growth factor (PDGF), epidermal growth factor (EGF), transforming growth factor beta (TGF-β), basic fibroblast growth factor (bFGF), thymosin α1 (Tα1) and vascular endothelial growth factor (VEGF). More preferably, the agent is transforming growth factor beta (TGF-β) or other members of the TGF-β superfamily.

In another embodiment of the invention, the composition of the invention further comprises an haemostatic substance, a growth factor, an anti-infective substance, an analgesic substance, an anti-inflammatory substance or a combination thereof.

The technology provided herein is not limited to the particular methodologies, protocols, constructs, formulae and reagents described but further include those known to the skilled artisan. It is also to be understood that the terminology used herein is for the purpose of describing particular embodiments only, and is not intended to limit the scope of the technology provided herein.

EXAMPLES

Materials and Methods

Materials
Culture Medium and Reagents

The culture medium EGM-2MV was from Lonza (Verviers, Belgium). Calcium- and Magnesium-free PBS, trypsine-EDTA (Versene), IPTG (Isopropyl-1-B-D-thio-1-galactopyranoside), kanamycine and chloramphenicol were purchased from Eurobio (Les Ulis, France).

Matrigel was purchased from Becton Dickinson (Le Pont de Claix, France).

Bacterial culture medium LB, Thermoscript and the high fidelity Platinum HIFI enzymes were obtained from Invitrogen (Cergy Pontoise, France).

Rneasy mini kit, Qiaquick and Qiaprep miniprep were obtained from Qiagen (Courtaboeuf, France), from Roche Applied Science and the kit RACE 5'3' RACE kit from Roche Applied Science.

Vascular endothelial growth factor (VEGF), fibroblast growth factor-2 (FGF2), and Interferon gamma (INFγ) were purchased from R&D (Abingdon, UK). The cloning vector pGEM-T easy vector and the expression vector pCi neovector were purchased from Promega (Charbonnières-les-bains, France), while the vector pET30 was from Novagen-Merck bioscience (Nottingham, United Kingdom distributed by VWR INTERNATIONAL S.A.S, Fontenay sous Bois, France).

Human VEGFA Sandwich ELISA kit was purchased from Cell Signaling technology.

Peptides

Peptides 7, 10, 11, 7B, 7A and 7C were chemically synthesized by GeneCust with N-terminal acetylation and C-terminal amidation as chemical modifications. All peptides were subjected to HPLC-purification step and funshed as lyophilized powder with at least 95% of purity.

Animals

Five-week old specific pathogen-free female Swiss Nude mice (weight 19 to 22 g), were purchased from Charles River laboratories (69592 L'Arbresle, France). Animals were housed in our animal care facilities until sacrifice. The animal care facility (CERFE, Evry, France) is certified by the French Ministry of Agriculture and Research. Animal experiments were performed according to ethical guidelines of animal experimentation (Directive n° 86/609 CEE) and the English guidelines for welfare of animals in experimental neoplasia (United Kingdom co-coordinating committee on cancer research guidelines for welfare of animals in experimental neoplasia (1998). Br. J. Cancer. 77:1-10).

Methods

Peptide Synthesis

All the peptides were synthesized chemically followed by an HPLC purification step ensuring at least 90% of purity of the purified peptide.

Angiogenesis Assay

Angiogenesis of human microvascular endothelial cells (HMEC) was induced in vitro using a Matrigel assay described by Grant et al (1989, Cell, 1989; 58:933). This method is based on the differentiation of endothelial cells to form capillary structures on a Matrigel Matrix. Matrigel is prepared the Engelbreth-Holm-Swarm (EHS) mouse tumor, which represents a complex mixture of basement membrane proteins including type IV collagen, entactin, proteo-heparan sulfate and other growth factors.

Briefly, 250 μl of Matrigel were transferred to each well of a 24-well culture plate and incubated at 37° C. for 30 min to allow for the matrix solution to solidify. HMEC grown in complete growth medium EGM-2MV were harvested by trypsin, suspended in the same growth medium and 500 μl containing 70 000 cells were added on top of the solidified Matrigel in each well and in the presence or absence of protein. Cells were maintained in a humidified atmosphere air containing 5% CO2 at 37° C. for 18-24 hrs. Endothelial tube formation was observed and photographed under an inverted light microscope.

Real-Time Reverse Transcription-Polymerase Chain Reaction Assay.

After exposure to the indicated concentrations of peptide 7 or peptide 10 issued from the recombinant protein GS-156A or vehicle for 24 h, HMEC ($5\times10^5$ cells/ml), total mRNA were isolated using NucleoSpin RNA II kit. RNA yields and purity were assessed by spectrophotometric analysis. The real-time RT-PCR was performed as previously described (Voghel et al., 2008). Briefly, 0.5 μg total RNA was reverse transcriped with random hexamer primers and M-MLV (200 U, Invirogen), and the synthesized cDNA was used immediately for real-time PCR amplification using the DNA-binding dye SYBR Green I for the detection of PCR products and the following primers: for VEGF-A (sense, 5' GAGGGCA-GAATCATCACGAA-3' (SEQ ID NO: 7); antisense, 5'-TGCTGTCTTGGGTGCATTGG-3' (SEQ ID NO: 8)); for GAPDH (sense, 5'-TGAAGGTCGGAGTCAACGGA-3' (SEQ ID NO: 9); antisense 5'-CATTGATGACAAGCTTC-CCG-3' (SEQ ID NO: 10)). The real-time PCR reactions were carried out with the DNA Engine OPTICON 2 continuous fluorescence detector (MJ Research, Waltham, Mass., U.S.A.). The results were quantifyed using the equation: CopyTF:CopyGAPDH=2C(t)GAPDH-C(t)TF. All PCR products were analyzed by electrophoresis on a 1.5% agarose gel, visualized with ethidium bromide, and analyzed using

| Peptide # | Sequence | MW (Da) | Isoelectric point | Chemical modification* |
|---|---|---|---|---|
| 7 | TQECPVRTSLDRELDLQASL | 2315.60 | 4.05 | N-acetylation & C-amidation |
| 10 | VSKDVCRL | 960.16 | 10.09 | N-acetylation & C-amidation |
| 11 | QSQKVPRQVQS | 1325.50 | 11.45 | N-acetylation & C-amidation |
| 7A | TQECPVRTSLD | 1289.39 | 4.05 | N-acetylation & C-amidation |
| 7B | ELDLQASL | 929.01 | 3.10 | N-acetylation & C-amidation |
| 7C | RRTTQECPVRTSLD | 1702.88 | 10.81 | N-acetylation & C-amidation | the Genesnap 6.00.26 software (Syngene, Cambridge, U.K.). Densitometric analysis was performed using GeneTools Analysis Software Version 3.02.00 (Syngene).
Protein Quantification.

Serum-deprived HMEC were incubated with different concentrations of peptide 7 or peptide 10 or vehicle for 24 h at 37° C. under 5% $CO_2$ for 6 h. After 3 washes with ice-cold PBS, cells were suspended with the protein extraction buffer (PEB) (20 mM Tris-HCl pH 7.5, 150 mM NaCl, 1 mM EDTA, 1 mM EGTA, 1% Triton, 25 mM sodium pyrophosphate, 1 mM β-glycero-phosphate, 1 mM Na3Vo4, 1 μg/ml leupeptine, 1 μM PMSF). The protein content was measured by Bradford. VEGFA concentration in the culture medium or in the extracts was determined by human VEGFA Sandwich ELISA kit (Cell Signaling technology) according to the manufacturer's instructions.
Activation Status of Protein Kinase B (pAkt) and the Mitogen Activated Protein Kinases (MAPK)

The activation status of pAkt was determined by western-blot using an anti-phosphoserine 473 pAkt antibody, and anti-GAPDH mAb as internal standard.

The activation status of MAPK was determined by western-blot using an anti-activated MAPK (pErk1/2) antibody, and anti-GAPDH mAb as internal standard.
Administration Route of the Peptides and Dosing The vehicle (Batch A) was administered by topical application at a standardized volume of 10 ml/kg for all applications. The peptides of the invention were administered by topical application at the concentration of 0.5 mg/ml in the vehicle. The protocols of treatment were as it follows:

Group 1: (Batch A, Vehicle): 1 topical application 10 minutes after wounding
Group 2: (Peptide 7, 0.5 mg/ml): 1 topical application 10 minutes after wounding
Group 3: (Peptide 10, 0.5 mg/ml): 1 topical application 10 minutes after wounding
Group 4: (Peptide 11, 0.5 mg/ml): 1 topical application 10 minutes after wounding
Group 5: (Peptide 7B, 0.5 mg/ml): 1 topical application 10 minutes after wounding.
Group 6: (Peptide 7A, 0.5 mg/ml): 1 topical application 10 minutes after wounding.
Group 7: (Peptide 7C, 0.5 mg/ml): 1 topical application 10 minutes after wounding.

Wounding

Healthy female BALBC Swiss mice were anesthetized by IP injection of Ketamine-Xylazine (80 mg/kg-12 mg/kg; Ref. K-113, Sigma, France). Two trans-dermal wounds, each of 5 mm in width and about 1 to 2 mm in depth were realized in the right and the left flanks of each mouse using 5 mm punch. Mice were observed for 2 h post-wounding.
Treatment Schedule At D1, and 10 min post-injury of the animals, the mice were randomized into 7 groups of 3 mice each.

All treatments were realized by topical application at the frequency of 1 topical application/day, for 4 days. Animals of group 1 were treated with the vehicle solution (Batch A). Animals of groups 2 to 7 were treated with the indicated peptide at a dose of 5 mg/kg.

Mice were treated for observed for 2 h post-treatment.

Ketamine/Xylazine (80 mg/kg-12 mg/kg; Ref. K-113, Sigma, France) was used to anaesthetize the animals before sacrifice by cervical dislocation.
Results
The Peptides of the Invention Induce In Vitro Angiogenesis The designed small peptides 7 (SEQ ID NO: 1), 10 (SEQ ID NO: 3), and 11 (SEQ ID NO: 4) were synthesized and tested for their in vitro angiogenesis-inducing activities (as described in Methods here above).

Figure 1:
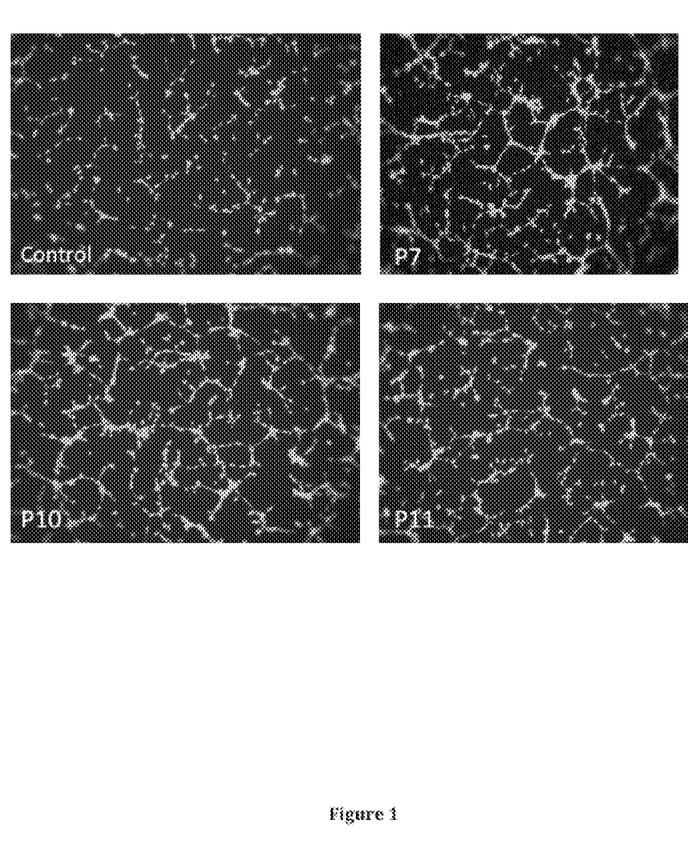
FIG. 1: Representative images of the in vitro angiogenesis assay in presence of peptide 7, 10 and 11 (images were taken at 6 h post incubation).

The results of the in vitro angiogenesis assay were presented in FIG. 1, using HMEC and 400 μg/ml final concentration of each peptide. Images were taken at 6 h post incubation.

These results show that peptides 7, 10, and 11 have a strong in vitro angiogenesis-inducing activity, and the in vitro angiogenesis inducing activity of these peptides can be classified as follow; peptide 7>peptide 10>peptide 11.
Wound Healing with Peptide 7

Figure 2:
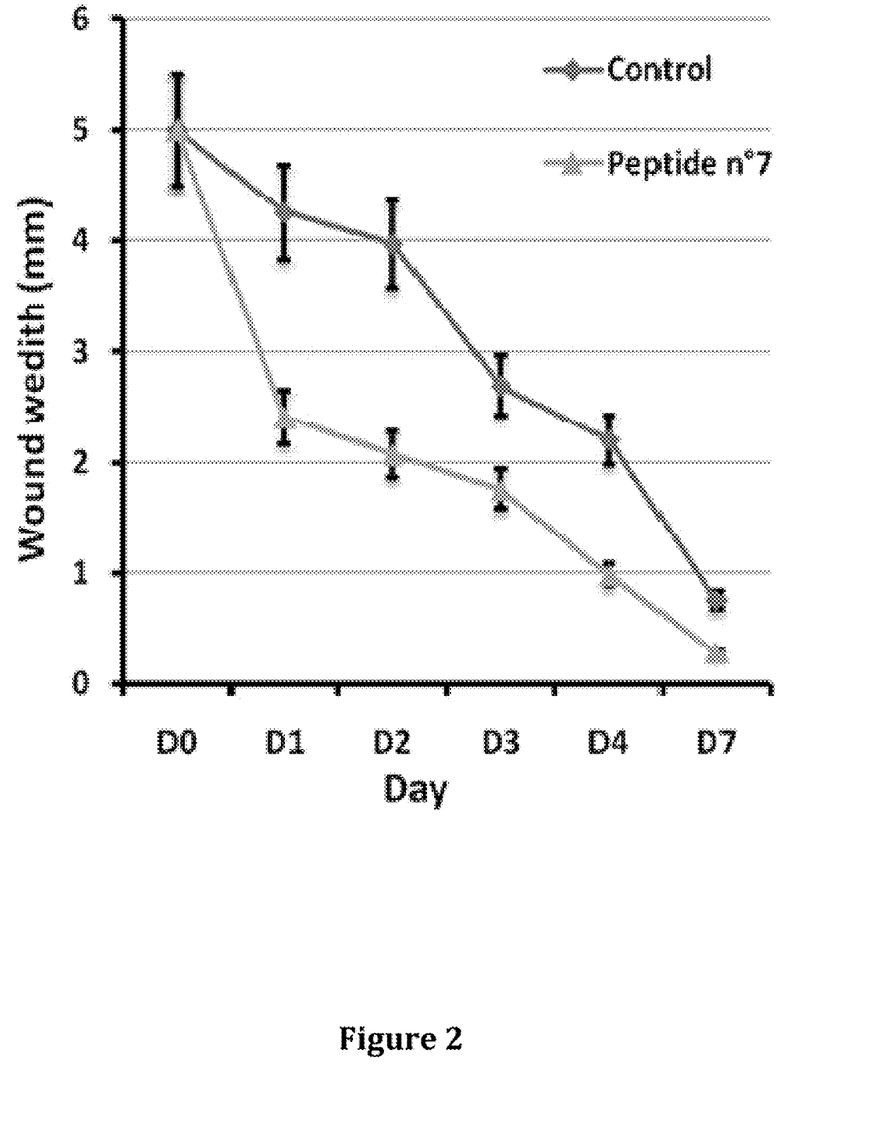
FIG. 2: Time course of wound healing of Vehicle treated wounds and peptide 7 treated wounds.

The examination of wound healing post treatment with the peptide 7 showed that the wounds treated with this peptide healed faster than the wounds treated with Vehicle (FIG. 2). At day 1, 2, 3 and 4 post treatment, the vehicle treated wounds showed 16.9, 21.2, 45.9, and 57.5% healing respectively, while the wounds treated with peptide n° 7 showed 52.8, 60.1, 65.6, and 82.9% healing at day 1, 2, 3 and 4 post treatment respectively.
Wound Healing with Peptide 10

Figure 3:
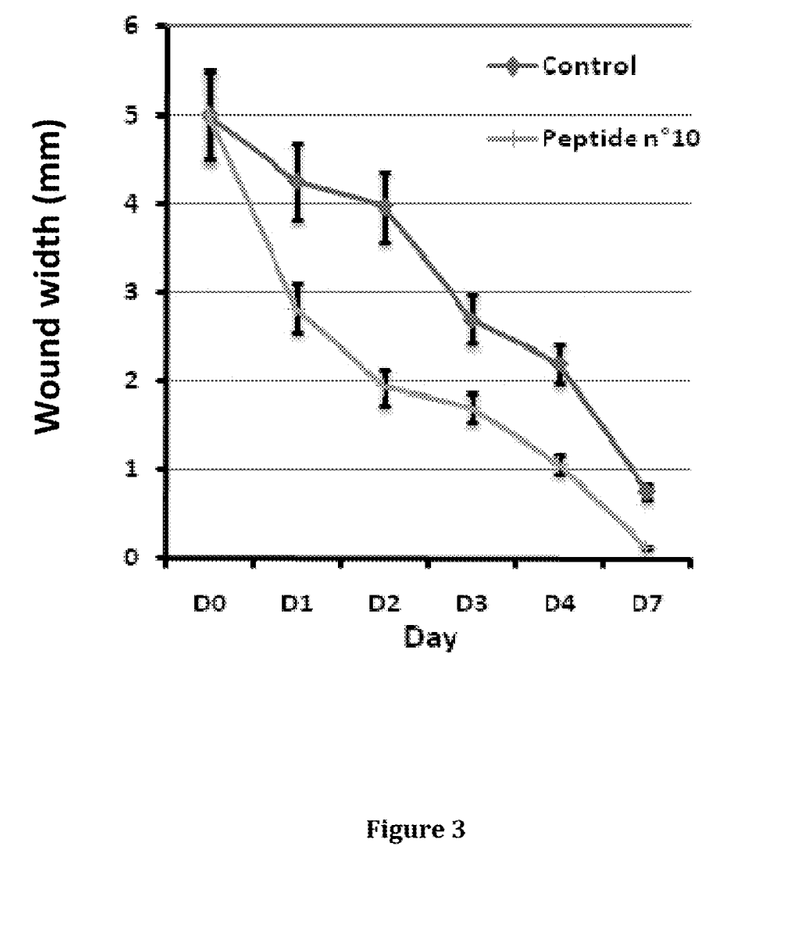
FIG. 3: Time course of wound healing of Vehicle treated wounds and peptide 10 treated wounds.

The examination of wound healing post treatment with the peptide 10 showed that the wounds treated with this peptide healed faster than the wounds treated with Vehicle (FIG. 3). At day 1, 2, 3 and 4 post treatment, the vehicle treated wounds showed 16.9, 21.2, 45.9, and 57.5% healing respectively, while the wounds treated with peptide 10 showed 42.8, 61.3, 65.6, and 78.9% healing at day 1, 2, 3 and 4 post treatment respectively.
Wound Healing with Peptide 11

Figure 4:
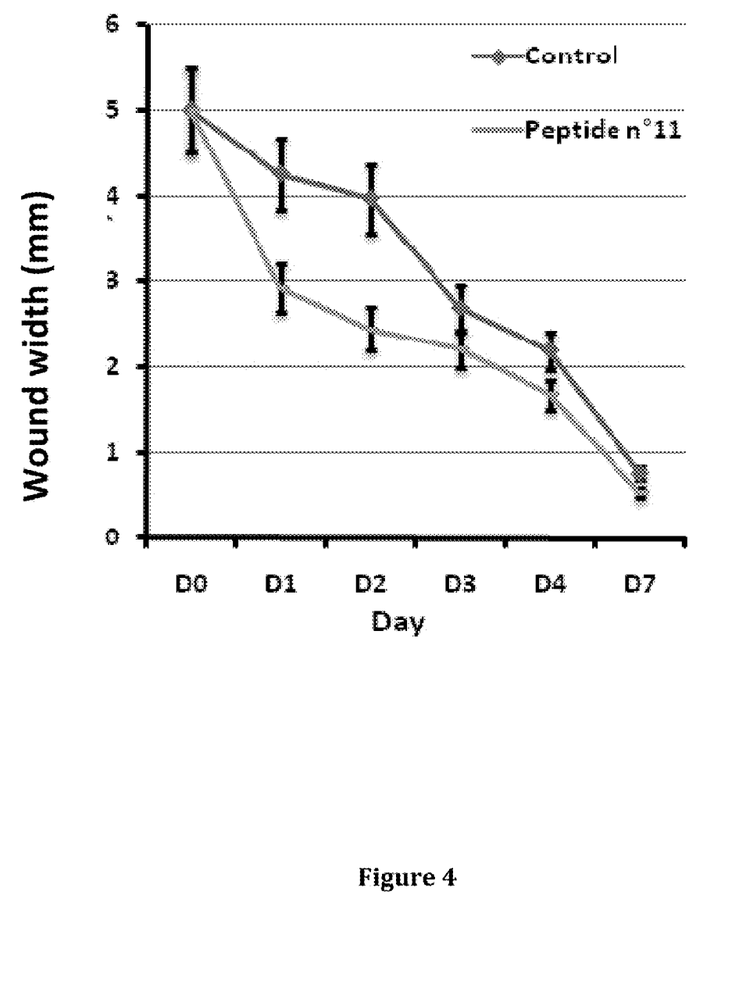
FIG. 4: Time course of wound healing of Vehicle treated wounds and peptide 11 treated wounds.
Figure 5:
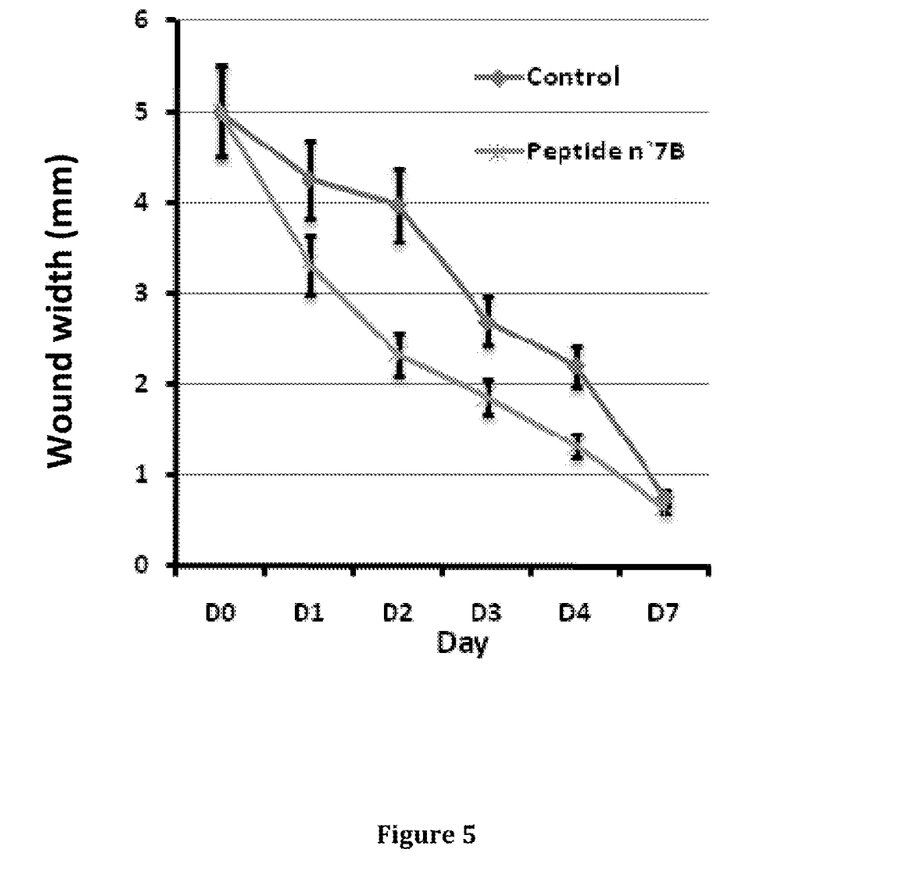
FIG. 5: Time course of wound healing of Vehicle treated wounds and peptide 7B treated wounds.
Figure 6:
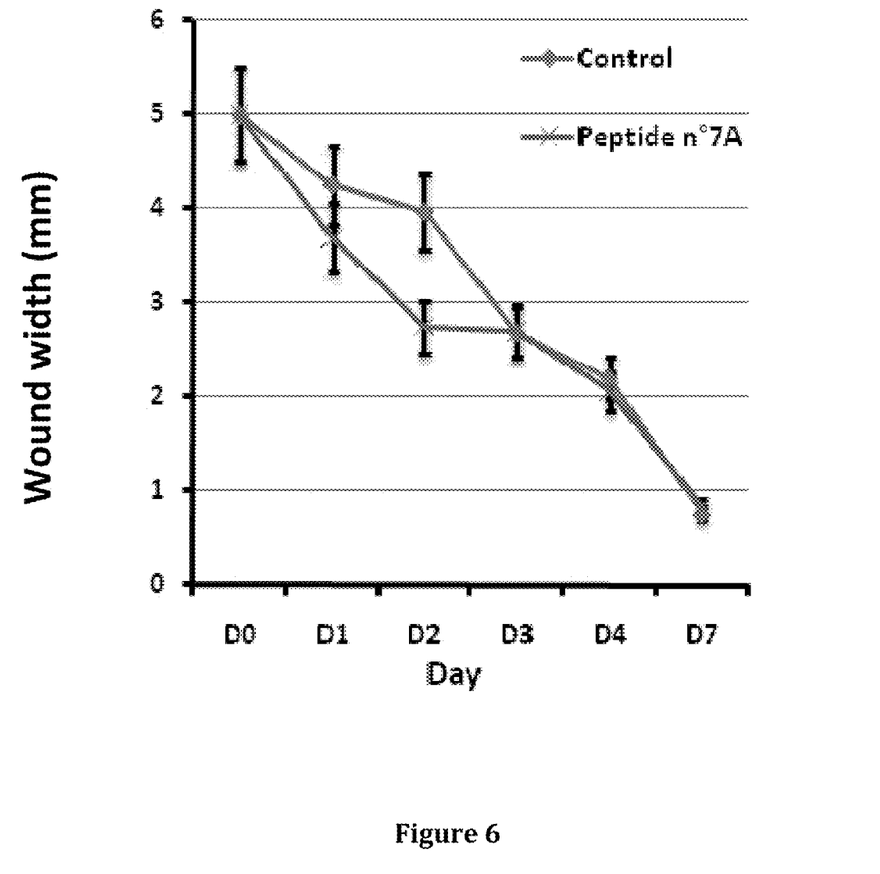
FIG. 6: Time course of wound healing of Vehicle treated wounds and peptide 7A treated wounds.
Figure 7:
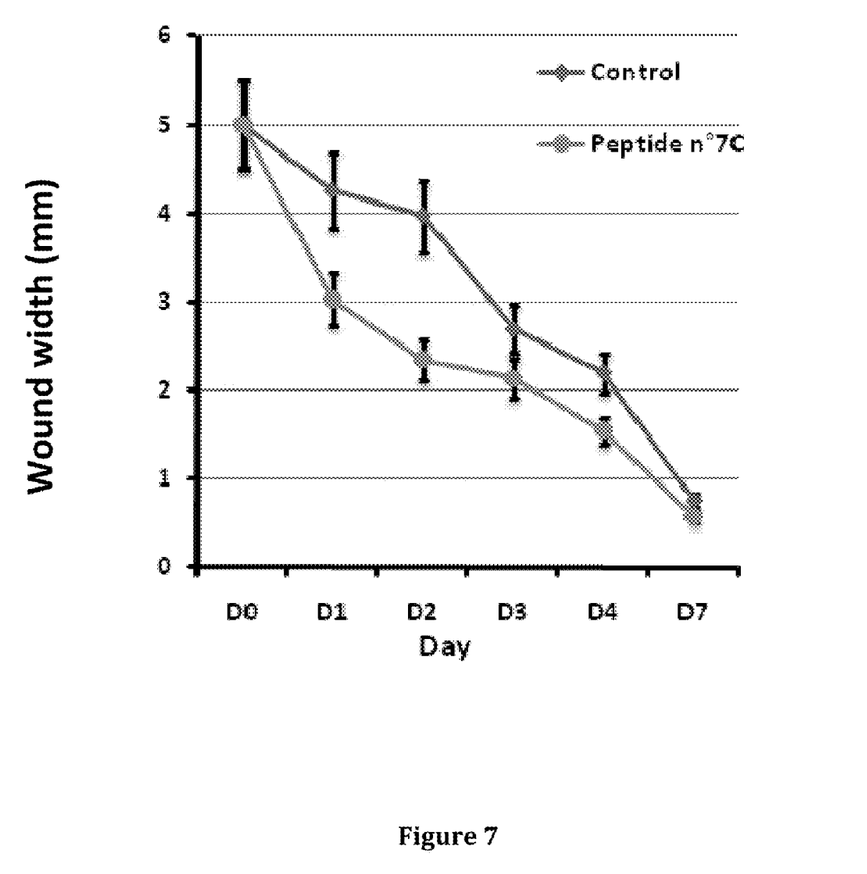
FIG. 7: Time course of wound healing of Vehicle treated wounds and peptide 7C treated wounds.

The examination of wound healing post treatment with the peptide 11 showed that the wounds treated with this peptide healed faster than the wounds treated with Vehicle (FIG. 4). At day 1, 2, 3 and 4 post treatment, the vehicle treated wounds showed 16.9, 21.2, 45.9, and 57.5% healing respectively, while the wounds treated with peptide 11 showed 41.9, 52.1, 58.4, and 64.4% healing at day 1, 2, 3 and 4 post treatment respectively.
Wound Healing with Peptide 7B The examination of wound healing post treatment with the peptide 7B showed that the wounds treated with this peptide healed faster than the wounds treated with Vehicle (FIG. 5). At day 1, 2, 3 and 4 post treatment, the vehicle treated wounds showed 16.9, 21.2, 45.9, and 57.5% healing respectively, while the wounds treated with peptide 7B showed 33.2, 56.9, 63.7, and 76.6% healing at day 1, 2, 3 and 4 post treatment respectively.
Wound Healing with Peptide 7A The examination of wound healing post treatment with the peptide 7A showed that the wounds treated with this peptide healed faster than the wounds treated with Vehicle (FIG. 6). At day 1, 2, 3 and 4 post treatment, the vehicle treated wounds showed 16.9, 21.2, 45.9, and 57.5% healing respectively, while the wounds treated with peptide n° 7A showed 27.4, 44.7, 45.1, and 58.8% healing at day 1, 2, 3 and 4 post treatment respectively.
Wound Healing with Peptide 7C The examination of wound healing post treatment with peptide 7C showed that the wounds treated with this peptide healed faster than the wounds treated with Vehicle (FIG. 7). At day 1, 2, 3 and 4 post treatment, the vehicle treated wounds showed 16.9, 21.2, 45.9, and 57.5% healing respectively, while the wounds treated with peptide n° 7C showed 39.4, 55.3, 58.8, and 68.2% healing at day 1, 2, 3 and 4 post treatment respectively.

Figure 8:
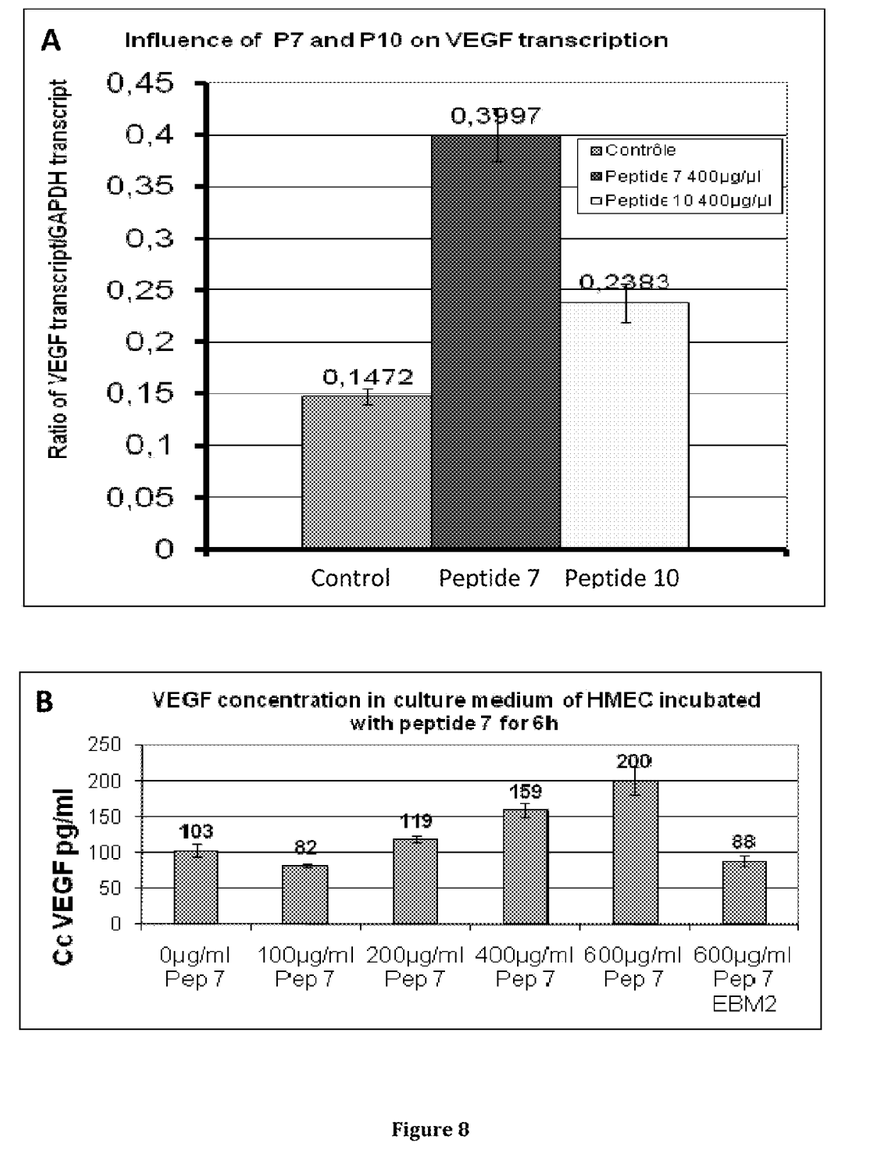
FIG. 8: (A) Measure of VEGF by QPCR in the presence of peptide 7 or peptide 10. (B) Measure of VEGF by ELISA in the presence of peptide 7.

Peptide 7 Induces VEGF Expression Both at the Transcriptional and Translational Levels in HMEC The influence of peptide 7 and peptide 10 on VEGFA expression was investigated. For that, HMEC were incubated with either peptide 7 (400 µg/ml final concentration), or peptide 10 (400 µg/ml final concentration) for 6 h, followed by measuring the expression of VEGFA by real time quantitative PCR (QPCR). Results showed that HMEC incubated with peptide 7 expressed about 170% higher VEGFA mRNA than HMEC incubated without addition of peptide (Control) (FIG. 8A). Results presented in the same FIG. 8 showed also that HMEC incubated with peptide 10 expressed about 60% higher VEGFA mRNA than HMEC incubated without addition of peptide (Control).

To show that this induced transcriptional expression of VEGFA could be found also at the translational level, we have used human VEGFA-specific sandwich ELISA assay to determine the concentration of VEGFA protein. Analysis of the culture medium of HMEC incubated with increasing concentrations of peptide 7 showed that there are dose-dependent increase in VEGF protein within the culture medium reaching a peak of about 97% increase at 400 µg/ml of peptide 7 attesting that there are about 2-folds increases of VEGFA-biosynthesis and excretion (p<0.001) (FIG. 8B). These results indicate that the induced transcriptional expression of VEGFA induced by the peptide 7 could be found also at the translational level.

Peptide 7 and Peptide 10 Induce Protein Kinase B (Akt) Activation but not MAPK in HMEC.

Figure 9:
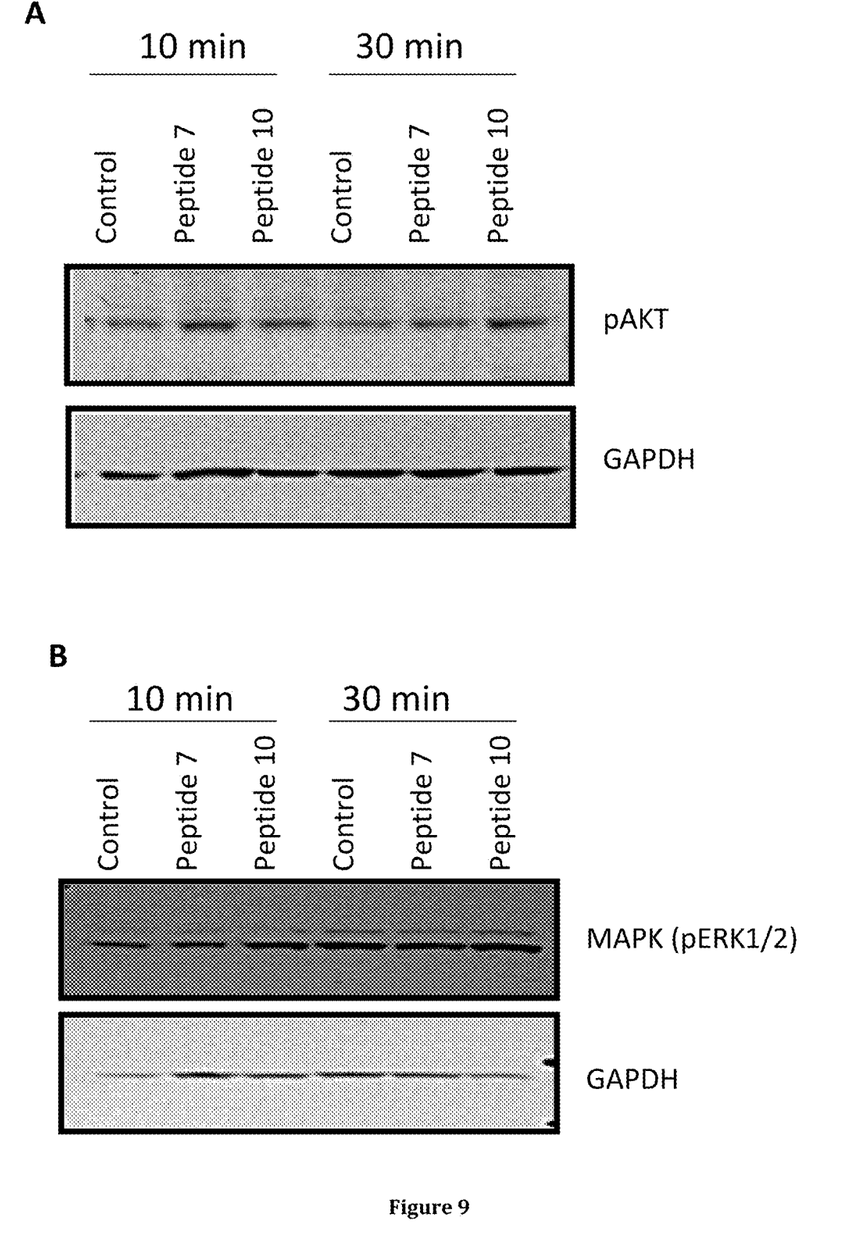
FIG. 9: (A) Influence of peptide 7 (400 µg/ml) and peptide 10 (400 µg/ml) onto pAkt activation. Immunoblot with anti-activated pAkt monoclonal antibody. and anti-GAPDH mAb as internal control. (B) Influence of peptide 7 and peptide 10 onto MAPK activation. A) Immunoblot with anti-activated MAPK (pErk1/2) monoclonal antibody and anti-GAPDH mAb as internal control.

The status of Akt in the HMEC following incubation with either peptide 7 or peptide 10 was investigated. Results showed that HMEC (control) posses a modest level of activated Akt (FIG. 9A, lane 1 and 4). HMEC cell lines incubated with peptide 7, however, present much higher level of activated Akt 10 min and 30 min post incubation (FIG. 9A, lanes 2 and 5 respectively) relative to the HMEC incubated without peptide (Control), indicating that the peptide 7 induces the activation of Akt.

The investigation of pAkt status in HMEC cell lines incubated with peptide 10 also showed that there is much higher level of activated Akt 10 min and 30 min post incubation (FIG. 9A, lanes 3 and 6 respectively) relative to the HMEC incubated without peptide (Control), indicating also that the peptide 10 induces the activation of Akt.

We have also investigated the status of the mitogen activated protein kinase (MAPK), as it is well established that it represents another cascade of intracellular signaling could be implicated in the regulation of VEGF expression. Results showed that there are not significant variations in level of activation of Erk1 and 2 (two members of MAPK) between HMEC incubated without peptide addition (Control), HMEC incubated with the peptide 7, HMEC incubated with the peptide 10 (FIG. 9B), indicating that neither the peptide 7 not peptide 10 could activate MAPK, and the MAPK cascade is seems to not implicated in the peptide 7- and peptide 10-induced expression of VEGF.

The invention claimed is:

1. A peptide consisting of 8 to 50 amino acids comprising a sequence selected from the group consisting of: SEQ ID NO: 1, SEQ ID NO: 2, SEQ ID NO: 3, SEQ ID NO: 4, SEQ ID NO: 5 and SEQ ID NO: 6.

2. The peptide according to claim 1, wherein the peptide consists of 8 to 30 amino acids.

3. The peptide according to claim 1, wherein said peptide is chemically modified by an acetylation and/or an amidation.

4. A composition comprising at least one of the peptides according to claim 1.

5. The composition according to claim 4, further comprising an haemostatic substance, a growth factor, an anti-infective substance, an analgesic substance, an anti-inflammatory substance or a combination thereof.

6. The composition according to claim 4, being in a form suitable for topical, oral or parenteral administration.

7. The composition according to claim 4, being in a form suitable for topical administration, wherein the form suitable for topical administration is lotion, salve, gel, cream, balsam, tincture, cataplasm, elixir, paste, spray, collyrium, drops, suspension, dispersion, hydrogel, ointment, emulsion or powder.

8. The composition according to claim 4, wherein the composition is a pharmaceutical composition comprising a pharmaceutically acceptable excipient.

9. The composition according to claim 4, wherein the composition is a cosmetic composition comprising a cosmetically acceptable carrier.

10. The composition according to claim 4, wherein the peptide is present in an amount of 0.01 to 5 mg per milliliter of composition.

11. A method for healing a wound in a subject in need thereof, comprising administering to the wound site an effective amount of a peptide consisting of 8 to 50 amino acids comprising a sequence selected from the group consisting of: SEQ ID NO: 1, SEQ ID NO: 2, SEQ ID NO: 3, SEQ ID NO: 4, SEQ ID NO: 5 and SEQ ID NO: 6.

12. The method according to claim 11, wherein the wound is an open wound.

13. The method according to claim 11, wherein the wound is a closed wound.

14. The method according to claim 11, wherein the wound is an acute or a chronic wound.

15. A medical device comprising a peptide consisting of 8 to 50 amino acids comprising a sequence selected from the group consisting of: SEQ ID NO: 1, SEQ ID NO: 2, SEQ ID NO: 3, SEQ ID NO: 4, SEQ ID NO: 5 and SEQ ID NO: 6.

16. The medical device according to claim 15, being in the form of a bandage, gauze, wound or sore dressing, dermal patch, or adhesive tape.

* * * * *